United States Patent
Holdaway et al.

Patent Number: 6,083,166
Date of Patent: Jul. 4, 2000

[54] METHOD AND APPARATUS FOR DETERMINING A MEASURE OF TISSUE MANIPULATION

[75] Inventors: Charles Holdaway, San Diego; David G. Matsuura, Escondido; Paul F. Zupkas, San Diego, all of Calif.

[73] Assignee: Situs Corporation, Solana Beach, Calif.

[21] Appl. No.: 08/982,753

[22] Filed: Dec. 2, 1997

[51] Int. Cl.⁷ .................................................. A61B 17/00
[52] U.S. Cl. ................. 600/439; 606/21; 606/28
[58] Field of Search .................... 600/439; 601/1–3; 606/20, 21, 22, 23, 24, 25, 26, 27, 28; 607/102, 104, 105

[56] References Cited

U.S. PATENT DOCUMENTS

| | | | |
|---|---|---|---|
| 3,556,079 | 1/1971 | Omizo | 128/2 |
| 3,911,924 | 10/1975 | Zimmer | 128/303.1 |
| 3,933,156 | 1/1976 | Riggi | 128/303.1 |
| 3,942,530 | 3/1976 | Northeved | 128/303.15 |
| 3,948,269 | 4/1976 | Zimmer | 128/303.1 |
| 3,971,383 | 7/1976 | van Gerven | 128/303.1 |
| 4,018,227 | 4/1977 | Wallach | 128/303.1 |
| 4,022,215 | 5/1977 | Benson | 128/303.1 |
| 4,029,102 | 6/1977 | Barger | 128/303.1 |
| 4,063,560 | 12/1977 | Thomas et al. | 128/303.1 |
| 4,082,096 | 4/1978 | Benson | 128/303.1 |
| 4,146,030 | 3/1979 | Holroyd | 128/303.1 |
| 4,206,609 | 6/1980 | Durenee | 62/6 |
| 4,206,760 | 6/1980 | Davis | 128/303.1 |
| 4,207,897 | 6/1980 | Lloyd et al. | 128/303.1 |
| 4,211,231 | 7/1980 | Rzasa | 128/303.1 |
| 4,236,518 | 12/1980 | Floyd | 128/303.1 |
| 4,249,536 | 2/1981 | Vega | 128/349 |
| 4,249,539 | 2/1981 | Vilkomerson et al. | 128/660 |
| 4,280,499 | 7/1981 | Sguazzi | 128/303.1 |
| 4,345,598 | 8/1982 | Zobac et al. | 128/303.1 |
| 4,377,168 | 3/1983 | Rzasa et al. | 128/303.1 |

(List continued on next page.)

FOREIGN PATENT DOCUMENTS

| | | |
|---|---|---|
| 0 329 492 A2 | 8/1989 | European Pat. Off. . |
| 0 446 645 A1 | 9/1991 | European Pat. Off. ........ A61B 8/12 |
| 0 873 722 A1 | 10/1998 | European Pat. Off. . |
| WO 96/05768 | 2/1996 | WIPO . |
| WO 97/01988 | 1/1997 | WIPO . |
| WO 97/29699 | 8/1997 | WIPO . |
| WO 98/30144 | 7/1998 | WIPO . |

OTHER PUBLICATIONS

Boring, C.C. et al. (1993) Cancer Statistics, 1993. CA Cancer Journal for Clinicians 42(1):7–26.

Coleman, D.J., et al. (1986) Therapeutic Ultrasound. Ultrasound in Med. & Biol. 12:633–638.

DeReggi, A.S., et al. (1981) Piezoelectric polymer probe for ultrasonic applications. J. Acoust. Soc. Am. 69:854–859.

(List continued on next page.)

*Primary Examiner*—Marvin M. Lateef
*Assistant Examiner*—Shawna J. Shaw
*Attorney, Agent, or Firm*—Knobbe, Martens, Olson & Bear, LLP

[57] ABSTRACT

A surgical device is comprised of a probe adapted for insertion into a patient. The probe has a means for manipulating tissue within a zone of manipulation. The probe also has a first receiver which is disposed within the zone of manipulation. The first receiver responds to receipt of a radiated signal by generation of a first receiver signal indicating a strength at which the radiated signal is received. A means for analyzing the first receiver signal determines a measure of manipulation to the tissue within the zone of manipulation. In one embodiment, the first receiver is disposed at the tip of the probe. In another embodiment, the means for manipulating removes energy from the tissue. In yet another embodiment, the means for manipulating adds energy to the tissue so as to alter the tissue. Optionally, the means for analyzing accumulates a set of values of the first receiver signal over time in order to determine the measure of manipulation. A scanner generates the radiated signal. Optionally, the scanner is an ultrasonic scanner and the radiated signal is an ultrasonic signal.

31 Claims, 7 Drawing Sheets

U.S. PATENT DOCUMENTS

| | | | |
|---|---|---|---|
| 4,407,294 | 10/1983 | Vilkomerson | 128/660 |
| 4,412,248 | 10/1983 | Carmen | 358/112 |
| 4,416,281 | 11/1983 | Cooper et al. | 128/400 |
| 4,431,006 | 2/1984 | Trimmer et al. | 128/660 |
| 4,697,595 | 10/1987 | Breyer et al. | 128/660 |
| 4,698,595 | 10/1987 | Röschmann | 324/313 |
| 4,706,681 | 11/1987 | Breyer et al. | 128/642 |
| 4,869,259 | 9/1989 | Elkins | 128/660 |
| 4,946,460 | 8/1990 | Merry et al. | 606/24 |
| 5,010,886 | 4/1991 | Passafaro et al. | 128/660.03 |
| 5,042,486 | 8/1991 | Pfeiler et al. | 128/653 R |
| 5,078,713 | 1/1992 | Varney | 606/23 |
| 5,084,044 | 1/1992 | Quint | 606/27 |
| 5,108,390 | 4/1992 | Potocky et al. | 606/21 |
| 5,147,355 | 9/1992 | Friedman et al. | 606/23 |
| 5,161,536 | 11/1992 | Vilkomerson et al. | |
| 5,174,296 | 12/1992 | Watanabe et al. | 128/662.06 |
| 5,178,148 | 1/1993 | Lacoste et al. | 128/660.03 |
| 5,197,476 | 3/1993 | Nowacki et al. | 128/660.03 |
| 5,199,419 | 4/1993 | Remiszewski et al. | 128/20 |
| 5,211,165 | 5/1993 | Dumoulin et al. | 128/653.1 |
| 5,215,092 | 6/1993 | Wray | 128/660.09 |
| 5,234,004 | 8/1993 | Hascoet et al. | 607/116 |
| 5,243,988 | 9/1993 | Sieben et al. | 128/662.06 |
| 5,247,938 | 9/1993 | Silverstein et al. | 128/662.03 |
| 5,254,116 | 10/1993 | Baust et al. | 606/23 |
| 5,259,384 | 11/1993 | Kaufman et al. | 128/660.01 |
| 5,259,837 | 11/1993 | Van Wormer | 604/96 |
| 5,275,166 | 1/1994 | Vaitekunas et al. | 128/660.03 |
| 5,282,472 | 2/1994 | Companion et al. | |
| 5,295,484 | 3/1994 | Marcus et al. | 128/660.03 |
| 5,307,816 | 5/1994 | Hashimoto et al. | |
| 5,313,950 | 5/1994 | Ishikawa et al. | 128/662.06 |
| 5,325,860 | 7/1994 | Seward et al. | 128/662.06 |
| 5,370,121 | 12/1994 | Reichenberger et al. | 128/660.02 |
| 5,385,544 | 1/1995 | Edwards et al. | |
| 5,398,690 | 3/1995 | Batten et al. | |
| 5,433,717 | 7/1995 | Rubinsky et al. | 606/20 |
| 5,472,405 | 12/1995 | Buchholz et al. | 601/2 |
| 5,474,071 | 12/1995 | Chapelon et al. | |
| 5,531,742 | 7/1996 | Barken | 606/21 |
| 5,564,423 | 10/1996 | Mele et al. | 128/660.02 |
| 5,588,432 | 12/1996 | Crowley | |
| 5,624,382 | 4/1997 | Oppelt et al. | 601/2 |
| 5,647,868 | 7/1997 | Chinn | 606/21 |
| 5,657,760 | 8/1997 | Ying et al. | |
| 5,672,172 | 9/1997 | Zupkas | |

OTHER PUBLICATIONS

Fleming, C. et al. (1993) A Decision Analysis of Alternative Treatment Strategies for Clinically Localized Prostate Cancer. JAMA 269(20):2650–2658.

Gage, A.A. (1992) Cryosurgery in the Treatment of Cancer. Gynecology & Obstetrics 174:73–92.

Hilaris, B.S. (1997) Brachytherapy in cancer of the prostate: An historical perspective. Seminars in Surgical Oncology 13:399–405.

Holm, H.H. (1997) The history of interstitial brachytherapy of prostatic cancer. Seminars in Surgical Oncology 13:431–437.

Hunt, J.W. et al., (1983) Ultrasound transducers for pulse–echo medical imaging. IEEE Transactions on Biomedical Engineering vol. BMI–30, No.8 453–481.

Klein, E.A. (1992) Prostate Cancer: Current Concepts in Diagnosis and Treatment. Cleveland Clinic Journal of Med. 59(4):383–389.

Littrup, P.J. et al. (1993) The Benefit and Cost of Prostate Cancer Early Detection. CA Cancer Journal for Clinicians 43(3):134–149.

Litwin, M.S. et al. Why Do Sicker Patients Cost More? A Charge–Based Analysis of Patients Undergoing Prostatectomy. Journal of Urology 149:84–88.

Meijer, S. et al. (1992) Cryosurgery for Locally Recurrent Rectal Cancer. European Journal of Surgical Oncology 18:255–257.

Mettlin, C. et al. (1993) Trends in Prostate Cancer Care in the United States, 1974–1990: Observations from the Patient Care Evaluation Studies of the American College of Surgeons Commssion on Cancer. CA Cancer Journal for Clinicians 43(2):83–91.

Nori, D., et al. (1997) Current issues in techniques of prostate brachytherapy. Seminars in Surgical Oncology 13:444–453.

Onik, G. et al. (1988) US Caracteristics of Frozen Prostate. Radiology 168:629–631.

Porter, A.T., et al. (1993) Prostate brachytherapy. Cancer supplement 71:953–958.

Schoenwald, J.S., et al. (1983) PVF2 transducers for acoustic ranging and imaging in air. Ultrasonics symposium 577–580.

Telang, D.J. et al. (1992) Radical Surgery in the Treatment of Localized Carcinoma of the Prostate. Henry Ford Hosp Med J 40(1 & 2):108–110.

Watson, L.R. (1997) Ultrasound anatomy for prostate brachytherapy. Seminars in surgical oncology 13:391–398.

White, J.R., et al. (1997) Bracytherapy and breast cancer. Seminars in surgical oncology 13:190–195.

Whitmore, W.F., Jr. (1993) Management of Clinically Localized Prostatic Cancer, An Unresolved Problem. JAMA 269(20):2676–2677.

Amertek Medical, Inc. (1998) Sure–Point stepping & stabilizing system for seed implantation http://www.amertekmed.com/image2.htm 6 pgs.

Kapton (1998) High performance films. http://www.kapton.com/indes.htm 6 pgs.

Flexible Circuitry information (1998) world wide web 9 pgs.

Vernitron (1984) Modern piezoelectric ceramics. PD 9247 1–8.

Blasko, J.C., et al. (1996) Should brachytherapy be considered a therapeutic option in localized prostate cancer? The urologic clinics of north America 23:633–650.

METHOD AND APPARATUS FOR DETERMINING A MEASURE OF TISSUE MANIPULATION

BACKGROUND OF THE INVENTION

I. Field of the Invention

The present invention relates to medical devices. More particularly, the present invention relates to a minimally invasive surgical procedures.

II. Description of the Related Art

The use of minimally invasive surgical techniques has dramatically affected the methods and outcomes of surgical procedures. Physically cutting through tissue and organs to visually expose surgical sites in conventional "open surgical" procedures causes tremendous blunt trauma and blood loss. Exposure of internal tissues and organs in this manner also dramatically increases the risk of infection. Trauma, blood loss, and infection all combine to extend recovery times, increase the rate of complications, and require a more intensive care and monitoring regiment. The result of such open surgical procedures is more pain and suffering, higher procedural costs, and greater risk of adverse outcomes.

In contrast, minimally invasive surgical procedures cause little blunt trauma or blood loss and minimize the risk of infection by maintaining the body's natural barriers to infection. Minimally invasive surgical procedures result in faster recoveries and cause fewer complications than conventional surgical procedures. Minimally invasive procedures, such as laparoscopic, endoscopic, or cystoscopic surgery, have replaced more invasive surgical procedures in all areas of medicine. Due to technological advancements in areas such as fiber optics, micro-tool fabrication, noninvasive visualization, and material science, the physician performing the operation has easier-to-operate and more cost effective tools for use in minimally invasive procedures. However, there still exist a host of technical hurdles that limit the efficacy and increase the difficulty of minimally invasive procedures.

One critical aspect of minimally invasive surgical techniques is the ability of the operator to visualize of the position of surgical instruments within the body and to determine the extent of the manipulation of organs and tissues caused by the surgical instruments. For example, percutaneous coronary angioplasty (PTCA) uses fluoroscopy to position a tiny balloon at the end of a long flexible catheter in a coronary artery where a stricture has reduced blood flow to the heart. Expanding the balloon at the site of the stricture opens the blocked arteries and normal blood flow returns. Visualization of the position of the balloon and the extent of tissue manipulation by the balloon is accomplished by injecting radiographic fluid through the catheter into the arteries. Thus, fluorscopy provides a detailed picture of the boundaries of the vessels to be treated, the position of the balloon within the vessel, and the extent and result of tissue manipulation by the balloon. Fluoroscopy is a critical aspect of the PTCA procedure because it provides the operator with a method for determining the exact position of the PTCA balloon in the artery and the effectiveness of the balloon in opening the stricture.

Another example of a minimally invasive procedure is arthroscopic surgery in which fiber optic visualization is used to position and control small tools within bone joints to repair, ablate, or remove tissue. Instruments, such as fiber optic scopes, small surgical tools and aspiration tubes, are placed in the joint through small skin incisions. The entire operation is performed by the operator visualizing the affected area through the fiber optic scope. Direct visualization is effective because the operator can expand the joint with a clear fluid and illuminate the surgical field.

Fiber optic and fluoroscopic visualization require a vessel, duct, or cavity into which a clear or radiopaque fluid can be injected. However, procedures not involving a vessel, duct, or cavity require other methods of visualization. For example, the manipulation of soft tissue organs requires entirely different methods of visualization. In such procedures, visualization techniques such as magnetic resonance imaging (MRI) or ultrasound which distinguish the borders and shapes of soft tissue organs or masses are required.

MRI has been particularly effective in providing detailed visualization of damage or growth of soft tissues surrounded by other organs and structures. MRI measures the radio frequency (RF) signals emitted by the nuclei of atoms subjected to a transient magnetic field while in a strong static field. These measurements define the nature and orientation of the atoms to provide a detailed image of the boundaries, geometry, and composition of tissues, organs or structures within the body. MRI's are routinely used to visualize herniated discs in the spinal cord, brain tumors, cancerous lesions deep within the body, and soft tissue damage to tendons and ligaments.

One prior art use for MRI is the visualization of the prostate and the progression of the growth of the iceball or frozen tissue surrounding a cryosurgical probe during the cryoablation of the prostate. MRI can be used to optimize probe placement and cooling parameters, to monitor the temperature distribution within the frozen region, and to determine the extent of tissue damage after the procedure. For an example of a procedure in this field, see U.S. Pat. No. 5,433,717 to Rubinsky et al. However, the size, cost, complexity, and nature of MRI systems may make them poor candidates for visualization in many surgical procedures.

Ultrasound imaging relies on the reflection of high frequency sound waves at interfaces of varying acoustic impedance to create a two dimensional picture of internal body structures. Present ultrasound imaging systems provide little detail and are limited by the sound transmission properties of obstructions in the field of view. Ultrasound provides a lower cost, less complicated and more compact alternative to MRI. Ultrasound imaging systems can typically be operated by one person, are a fraction of the cost and size of an MRI system, are mobile, and are less restrictive on the operating environnent.

The use of ultrasound in medicine is well documented and a considerable volume of patent literature exists describing designs, methods, and instrumentation in the area of ultrasound imaging and the use of ultrasound as a diagnostic or therapeutic tool. One application of ultrasound has been the evaluation of the structure and density of bone. For example, ultrasonic calipers containing an ultrasonic emitter and receiver have been used to measure the amplitude and velocity of an ultrasonic signal transmitted through bone tissue, such as the bone in a finger. The amplitude of the ultrasonic signal depends on the absorption of the ultrasound passing through the bone tissue. Other systems utilize a pair of ultrasound transducers, one emitting and the other receiving a composite sine wave acoustic signal consisting of repetitions of plural discrete ultrasonic frequencies spaced at discrete times. The signal is processed to determine a transfer function. The transfer function is then used to allow the evaluation of bone-related quantities such as bone density, bone strength, and fracture risk. For examples of patents in this area, see U.S. Pat. No. 5,564,423 to Mele et al. and U.S. Pat. No. 5,259,384 to Kaufman et al.

Modern ultrasound technology has expanded the application of minimally invasive surgical techniques into areas in which direct surgical intervention had previously been the only option. One surgical technique to which modern ultrasound imaging has been applied is cryosurgery. Cryosurgery involves the freezing of diseased tissue. Cryosurgery has been used for decades to destroy diseased tissue throughout the body. Historically, cryosurgery has been limited in its application to the destruction of tissue on the surface of the body or in a space where the visible manipulation of tissue was possible. Recently the role of cryosurgery has been expanded to include the application of cryosurgery in a minimally invasive manner. Minimally invasive techniques were made possible by the advances in the ability to visualize soft tissues by ultrasound imaging. Ultrasound imaging allows the surgeon to visualize "landmarks" within the patient and, thereby, correctly position the freezing probe or cryoprobe within the soft tissue.

Both heating and freezing of tissue affects its acoustic properties. In the case of heating and freezing tissue, the transmission of ultrasound signals through the tissue is affected by the change in density of water within the tissue. Although small, the change in density of water as a function of temperature is well documented. As an example, the density of water at 38 degrees Celsius is 0.99299 gm/ml and at 70 degrees Celsius is 0.97781 gm/ml. In the case of freezing, the density of ice is 0.9170 gm/ml. These density changes affect the attenuation of the ultrasound signal transmitted between the imaging system scanner and the probe transducer during the manipulation process.

An example of the application of cryosurgery in a minimally invasive manner is the destruction of diseased prostatic tissue using small diameter cryoprobes placed through the skin into the prostate. Ultrasound imaging allows the surgeon to view the prostatic margins, bladder, urethra, and rectum. Using these organs as "landmarks," the surgeon positions the cryoprobe within the prostate to optimally destroy the diseased tissue. Information concerning an ultrasound transducer which is attached to a cryoprobe can be found in U.S. patent application No. 08/468,717, filed Jun., 6, 1995, now issued as U.S. Pat. No. 5,672,172, entitled "SURGICAL INSTRUMENT WITH ULTRASOUND PULSE GENERATOR" which is assigned to the assignee of the present invention and which is incorporated herein by this reference. The patent describes a system and method which further enhances the ability of the surgeon to position the cryoprobe to optimally destroy diseased tissue by clearly marking the position of the tip of the cryoprobe in the display of an ultrasound imaging system.

Ultrasound imaging also provides the surgeon with a method for judging the extent of the manipulation by the cryoprobe. After positioning the cryoprobe within the desired tissue mass, the liquid nitrogen begins to flow to the cryoprobe. Tissue begins to freeze around the tip of the cryoprobe. As the flow of liquid nitrogen continues, thermal energy is removed from an expanding area of tissue surrounding the tip of the cryoprobe. The temperature profile of tissue manipulated by the cryoprobe is lowest at the tip and increases to the boundary of manipulated and unaffected tissue at normal body temperature. It is generally accepted that tissue destruction occurs at temperatures below minus 60 degrees Celsius, although such factors as the speed of freezing and thawing of the tissue and the water content of the tissue affect the temperature at which tissue destruction occurs.

Within this region of manipulated tissue is a boundary where the tissue temperature falls below 0 degrees Celsius. This area of frozen tissue is described as the "iceball." The boundary of the iceball is echogenic as a result of the difference in density between frozen and unfrozen tissue. As thermal energy is removed from the tissue and the iceball grows, the boundary appears as an expanding arc in the display of an ultrasound imaging system. Monitoring the growth and position of the arc gives the surgeon an indication of the extent of the manipulation of the tissue by the cryoprobe. However, as noted above, the actual destruction of tissue does not occur until the tissue reaches approximately minus 60 degrees Celsius. Therefore, the echogenic boundary is not directly indicative of the extent of tissue destruction. In addition, the ultrasound image provides the surgeon with no definite indication of the nature of the tissue within the iceball.

An alternative to the above description of a manipulation process employing cryosurgery is a manipulative process involving heating of tissue. In such a case, the manipulation tool is not a cryoprobe, but rather a probe to deliver microwave, RF, or other energy form that heats tissue. Such devices are commercially available and are presently used to ablate tissue of the prostate and endometrium. Heating tissue causes cell destruction leading to necrosis of tissue within a thermal zone surrounding the heating component. Just as in cryosurgery, monitoring of the effected zone is critical during the heating process to ensure destruction of all diseased tissue and the preservation of healthy surrounding tissue.

The surgical procedure for destroying a target tissue with a heating probe begins by placing the probe in the target tissue mass. Ultrasound imaging is typically used to guide the probe in a minimally invasive manner. An ultrasound transducer on the probe in close proximity to the heating element is used to facilitate the positioning of the probe. In similar fashion to the freezing probe ultrasound transducer, the heating probe ultrasound transducer generates an ultrasound signal. The signal is detected by the imaging system causing an indication to be displayed in the monitor of the imaging system at the ultrasound transducer on the probe. Thus, the imaging system defines the exact location of the probe tip and heating element. As the manipulation process heats tissue surrounding the probe tip, the ultrasound transducer continues to produce an image of the probe and surrounding tissue. Adding thermal energy to tissue changes the structure and density of the tissue, and, thus, affects the image seen by the surgeon. It is generally accepted that tissue can not tolerate temperatures greater than 60 degrees Celsius. However, the image created by an ultrasound scanner which is seen by the surgeon does not provide a definite indication of the boundary of the tissue which has reach 60 degrees Celsius. Thus, the surgeon is not provided with a good indication of the extent of tissue manipulation.

Therefore, it is apparent that there has been a long felt need in the industry to accurately determine the extent of tissue manipulation as a function of time. The present invention provides an elegant means and method for satisfying this need.

SUMMARY OF THE INVENTION

A surgical device is comprised of a probe adapted for insertion into a patient. The probe has a means for manipulating tissue within a zone of manipulation. The probe also has a first receiver which is disposed within the zone of manipulation. The first receiver responds to receipt of a radiated signal by generation of a first receiver signal indicating a strength at which the radiated signal is received. A means for analyzing the first receiver signal determines a measure of manipulation to the tissue within the zone of manipulation. In one embodiment, the first receiver is disposed at the tip of the probe. In another embodiment, the means for manipulating removes energy from the tissue. In yet another embodiment, the means for manipulating adds energy to the tissue. The means for manipulating may manipulate tissue by introduction of a substance or fluid. The means for manipulation may be implanted within the patient and may take the form of a bead. Optionally, the means for analyzing accumulates a set of values of the first receiver signal over time in order to determine the measure of manipulation. A scanner generates the radiated signal. Optionally, the scanner is an ultrasonic scanner and t radiated signal is an ultrasonic signal. The scanner may be disposed within the patient or external to the patient.

Optionally, a second receiver is also incorporated in the invention. The second receiver is separated from the first receiver so that the second receiver is disposed outside of the zone of manipulation. The second receiver responds to receipt of the radiated signal by generation of a second receiver signal.

The means for analyzing may have a means for detecting a relative movement between the probe and the scanner based on the second receiver signal. The means for analyzing may comprise an imaging system for displaying an image derived from signals generated by the scanner. The means for analyzing may further comprise a database comprising entries determined by empirical measurement and it may consult the database to determine the measure of manipulation. The means for analyzing may display a predication of the measure of manipulation. The means for analyzing may superimpose the prediction over the image derived from the signals generated by the scanner.

Alternatively, the means for analyzing may comprise a means for determining a distance between the scanner and the first receiver, a means for measuring an initial value of the first receiver signal, and a means for correlating the distance, the initial value of the first receiver signal and a subsequent value of the first receiver signal to determine the measure of manipulation. The means for correlating may comprise a database of entries determined from empirical data.

The present invention also envisions a method of determining a measure of manipulation. The method begins by disposing a manipulation probe within an area of tissue. A measurement of a signal strength of a radiated signal received at a receiver on the manipulation probe is taken. A determination of an extent of manipulation of the tissue is made based on the signal strength. The process of determining the extent of manipulation may be executed by determining a distance between a radiated energy source and the receiver of the probe. A measurement of an initial value of the signal strength is taken. A correlation of the distance, the initial value of the signal strength and a subsequent value of the signal strength is made in order to determine the extent of manipulation. Alternatively, correlation further comprises the step of consulting a database of entries determined from empirical data.

A radiation source may be inserted within a patient. An area of manipulation may be manipulated by introduction of a substance or a fluid. The method may comprise destruction of a portion of the area of tissue by addition of energy or by removal of energy. For example, diseased prostatic tissue may be destroyed. Further, a mechanical means may be used to manipulate the tissue. An image prediction of the extent of manipulation may be displayed. The display may show an image of the area of tissue derived from signals returning from a source of the radiated signal. An ultrasonic scanner disposed within the patient may be used to produce the radiated signal. Measurement of a signal strength of the radiated signal may be made at a point on the probe offset from the receiver so as to be outside of the area of tissue. Determination of a previous location of the probe may be made based on the signal strength of the radiated signal measured at the point on the probe offset from the receiver.

The present invention also envisions a method of accurately destroying diseased tissue in a non-invasive surgical procedure. A manipulative probe is inserted into a patient such that a manipulation means of the probe is disposed within a region of diseased tissue. A measurement is made of a signal strength of a radiated field within the region of diseased tissue. The region of diseased tissue is manipulated. The manipulation is terminated when the signal strength reaches a predetermined value.

The present invention also envisions, a device for correlation of image results to actual results in a system for manipulation. The device has a detector which detects a radiated signal. A manipulation generator is generally co-located with the detector. A series of measurement units are distributed at a variety of distances from the detector. The series of measurement units measures an indication of a degree of manipulation. A signal generator generates the radiated signal. A recording device is coupled to the series of measurement units and the detector. The detector, the manipulation generator and the series of measurement units are all disposed within a material having similar physical and chemical properties of tissue. The recording device is used to record input from the detector and the series of measurement units during destruction of the material by the manipulation generator.

BRIEF DESCRIPTION OF THE DRAWINGS

The features and advantages of the present invention will become more apparent from the detailed description set forth below when taken in conjunction with the drawings in which like reference characters correspond throughout and wherein.

DETAILED DESCRIPTION OF THE PREFERRED EMBODIMENT

Figure 1:
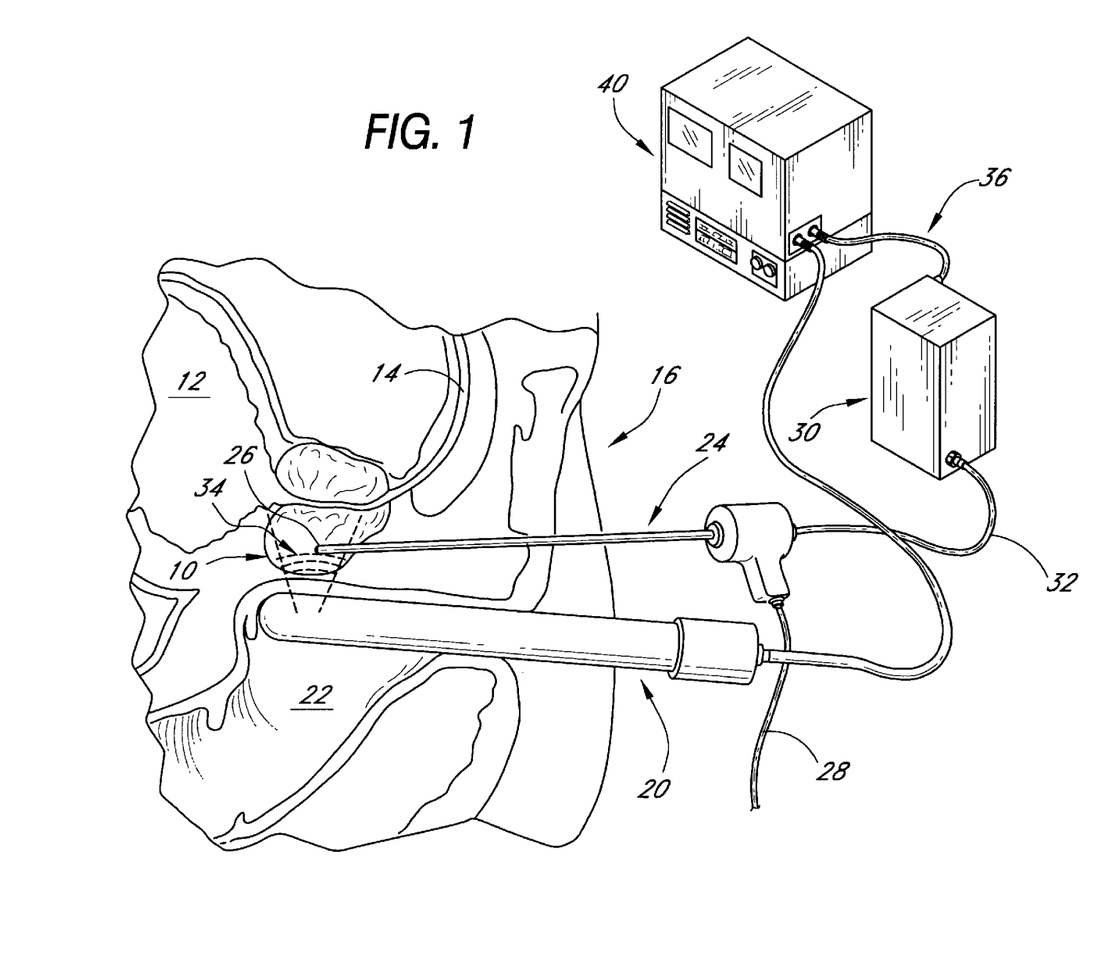
FIG. 1 is a perspective view of a configuration in accordance with the present invention portrayed as a cryosurgical probe placed within the prostate of a patient.

Referring now to FIG. 1, the present invention is shown in an exemplary application in which prostate tissue is thermally destroyed. The prostate 10 is located at the neck of the bladder 12 as it forms the urethra 14. A thermal manipulation probe 16 is inserted into the body and placed such that the tip of the probe 16 is located in a desired position within the prostate 10. The probe 16 may be properly placed in accordance with teachings in U.S. Pat. No. 5,672,172, incorporated herein above. A scanner 20 is placed in the rectum 22 and positioned such that an image of the prostate 10, the tip of the probe 16 and a portion of a shaft 24 of the probe 16 is displayed on an attached imaging and analysis system 40. In FIG. 1, we shall assume that the imaging and analysis system 40 combines the functions of the analysis function and the ultrasound imaging system, although these functions may be separated into two or more devices. Also in FIG. 1, we shall also assume that the scanner 20 transmits and receives ultrasound signals.

At the tip of the probe 16 is a chamber (not shown explicitly) into which a refrigerant fluid, typically liquid nitrogen or compressed gas, is pumped causing the freezing process. The refrigerant enters the chamber causing a reduction in temperature of the tip of the probe 16. When the freezing process begins, a zone of frozen tissue expands outward from the tip. The refrigerant is supplied to the probe 16 from a probe controller (not shown) through a refrigerant connector 28. The probe controller enables an operator to control the flow of refrigerant to the tip and, hence, the freezing effect of the probe tip.

In addition to the thermal expansion chamber, a receiver 26 is disposed at the tip of the probe 16. The receiver 26 is connected to a signal recovery unit 30 through a connector 32 The signal recovery unit 30 receives a response signal from the receiver 26 as a result of ultrasound signals received by the receiver 26 from the scanner 20. The signal recovery unit 30 uses the response signal to generate and generates a signal level indication which it passes over a connector 36 to the imaging and analysis system 40. The signal level indication reflects the value character of the response signal, i.e. amplitude, frequency, phased or shape, while maintaining a signal level and drive level usable by the imaging and analysis system 40. In the embodiment shown in FIG. 1, the imaging portion and the analysis portion of the apparatus are shown as co-located within a common housing while the recovery unit housed separately. Obviously, the teachings of the present invention are general and the common or disjoint housing of the components is irrelevant to the general teachings of the invention.

The scanner 20 radiates ultrasound signals 34 during the course of the tissue manipulation. The radiated signals 34 are reflected back to the scanner 20 from acoustic interfaces and are used to create an image which is displayed on the imaging and analysis system 40. The radiated signals 34 are also received by the receiver 26. In response to the signal level at which the radiated signals 34 reach the receiver 26, the receiver 26 generates the response signal which, in turn, determines the value of the signal level indication output by the signal recovery unit 30. As explained more fully below, the imaging and analysis system uses the signal level indication as well as other information to determine the extent of tissue manipulation.

Figure 2:
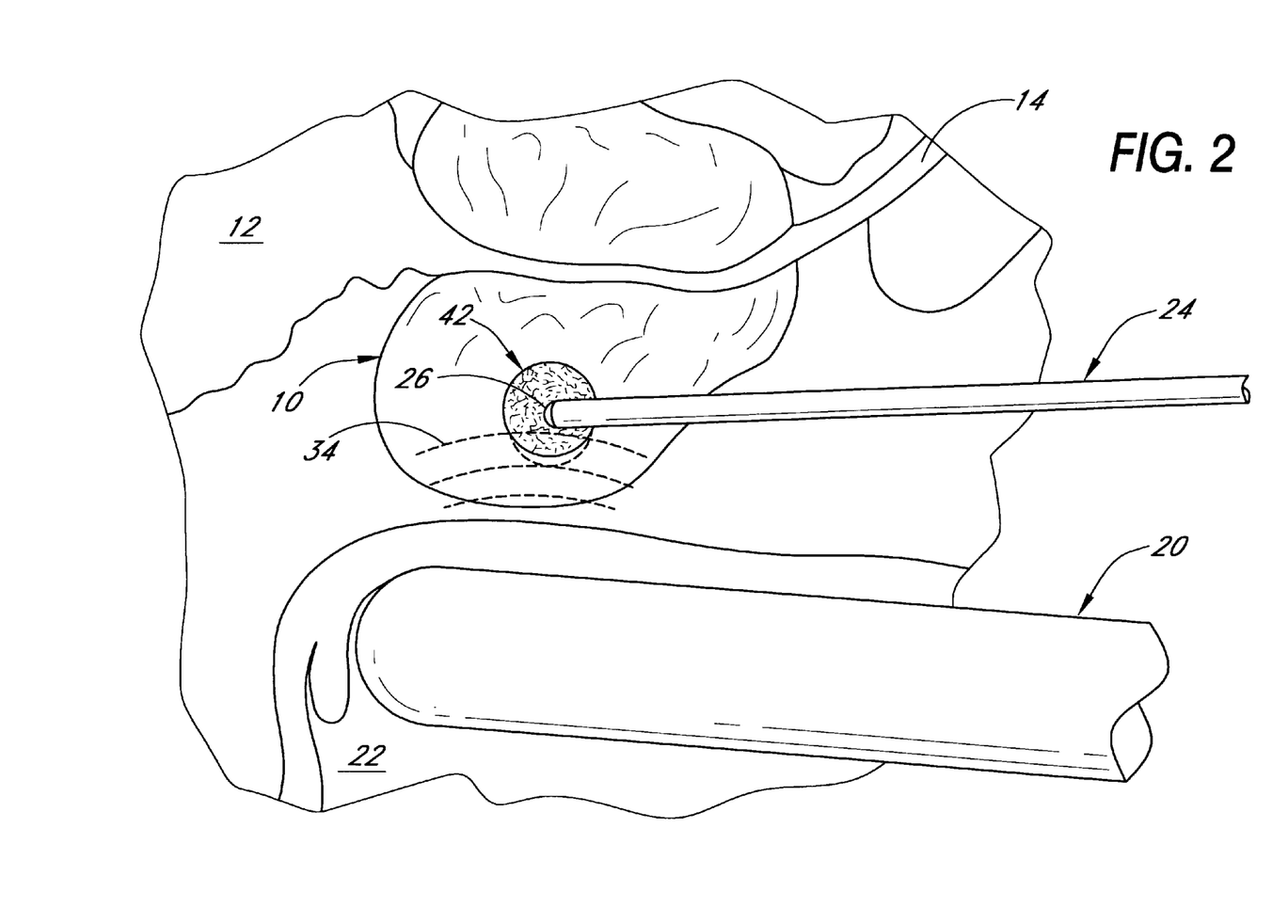
FIG. 2 is a perspective view of the probe and the resultant manipulated tissue during the surgical process.

Referring now to FIG. 2, the effect on the signal received by the receiver 26 due to the manipulation of tissue is illustrated. Before the manipulation process is begun, the radiated signals 34 pass through the prostate 10 and surrounding tissue from the scanner 20 to the receiver 26. As the manipulation process is begun, a zone of thermally manipulated tissue 42 is formed, as illustrated in FIG. 2. The radiated signals 34 must pass through the zone of thermally manipulated tissue 42 to reach the receiver 26. The manipulation process changes the transmission properties of the zone of manipulated tissue 42 as compared to the unmanipulated state. In turn, the signal level received at the receiver 26 also changes. As the manipulation process progresses and the size of the zone of manipulated tissue 42 grows, the signal level received by the receiver 26 continues to change.

Within the zone of manipulated tissue, there is a boundary where the temperature of the tissue falls below 0 degrees Celsius. The area in which the temperature of the tissue is less than 0 degrees Celsius is referred to as an "iceball." The boundary of the iceball is echogenic as a result of the difference in density between frozen and unfrozen tissue. The scanner 20 detects the boundary of the iceball within the zone of manipulated tissue 42. Therefore, as thermal energy is removed from the tissue and the zone of manipulated tissue expands, the iceball appears as an expanding arc in the display of an ultrasound imaging system. Because a significant amount of the radiated signal energy is reflected by the iceball surface and attenuated by the properties of the tissue within the iceball, the signal levels corresponding to reflections from within the iceball are small. Even though a detectable measure of signal energy may reach the tip of the probe 16, the echoed reflection is subjected to the same attenuation on the return path. If the attenuation from the scanner 20 to the tip of the probe 16 is 20 dB (a factor of 100), the echoed reflection reaches the scanner 20 attenuated by a factor of 10,000. Therefore, the character of the tissue within the iceball is difficult to detect with the scanner 20.

The actual destruction of tissue does not occur within the entire region of the iceball. As noted above, tissue destruction does not occur until the tissue reaches approximately minus 60 degrees Celsius. Therefore, within the iceball, there is a destruction region in which the tissue has been destroyed. The boundary of the scanned image indicates the boundary of the iceball but does not indicate the boundary of the destruction region.

During a non-invasive surgical procedure according to the preferred embodiment, the task of the surgeon is to destroy diseased tissue while leaving intact as much of the healthy surrounding tissue as possible. If the surgeon destroys healthy tissue, he may prolong the recovery of the patient as well as increase undesired side effects of the process. If the surgeon leaves a portion of the diseased tissue intact, he may increase the risk the diseased tissue will continue to spread or he may subject the patient to a subsequent surgical procedure. Therefore, it is extremely important the surgeon have an accurate indication of the degree of destruction of the diseased tissue. However, as noted above, the image of the iceball does not provide the surgeon with a definite indication of the extent of tissue destruction. Therefore, if the surgeon attempts to use the image of the iceball to estimate the destruction of tissue, he is likely to either destroy a significant amount of healthy tissue or to leave intact a portion of the diseased tissue. The present invention provides the surgeon with a more exact determination of the extent of destruction within the zone of manipulated tissue.

Figure 3:
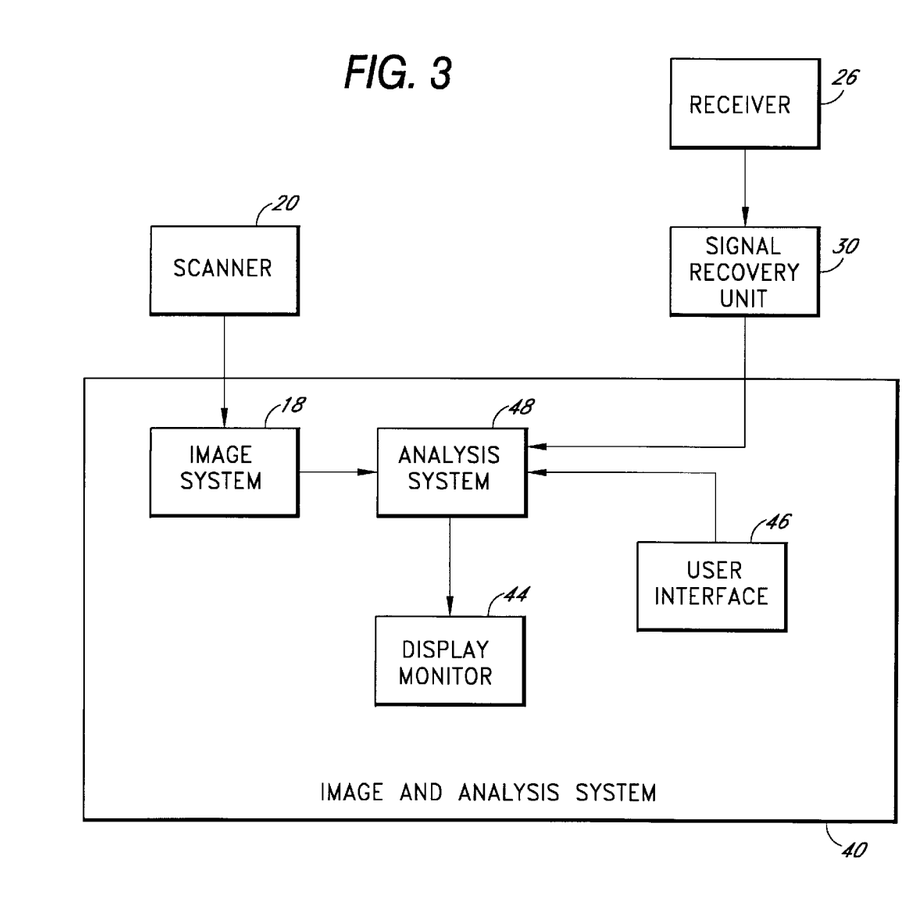
FIG. 3 is a block diagram showing the components of the invention.

FIG. 3 is a block diagram of the system of the present invention. The imaging and analysis system 40 receives input from the scanner 20. An imaging system 18 transforms the raw signaling into image data which is passed to an analysis system 48. The imaging and analysis system 40 also receives input from the receiver 26 via the signal recovery unit 30. As explained in greater detail below, the analysis system uses this data to determine a measure of manipulation. The results are displayed on a display monitor 44 which may take the form of a CRT, LED/LCD display, or other known output display means.

In the preferred embodiment, the imaging and analysis system 40 begins it analysis by determining a relative distance between the receiver 26 and the scanner 20. This measurement can be performed based on the standard image signals received from the scanner 20. The imaging and analysis system 40 also notes the level at which the receiver 26 receives the radiated signal as indicated by the signal level indication. Based on this information, the imaging and analysis system 40 can determine the initial characteristic of the tissue. Varying characteristics of tissues, such as water content, calcification and blood flow, cause the manipulation process to affect dissimilar types of tissue differently. The imaging and analysis system 40 must consider these differences.

The process of manipulating the tissue can now begin. As the tissue is manipulated, the image returned by the scanner 20 and the signal level indication begin to change. Based upon the changes in the signal level indication and the image, the imaging and analysis system 40 determines the extent of manipulation. In the preferred embodiment, the measure of manipulation which is being sought is the extent to which tissue has been destroyed. In the specific example above, destruction is caused by the fact the temperature of the tissue has fallen below a given level. Therefore, it is the task of the analysis system to determine a boundary where the temperature of the tissue has fallen below minus 60 degrees Celsius. The manipulation level which is sought may be entered by the operator using a user interface which may be soft key entry, a menu driven interface, a touch screen entry system, a mouse, keyboard or other interface means.

There are several ways which the analysis system 48 may correlate the incoming data to predict the measure of manipulation. For certain predictable environments, a transfer function may be developed. In other more complex environments, the analysis system 48 may use a database of empirical data to determine the extent of manipulation.

Figure 4:
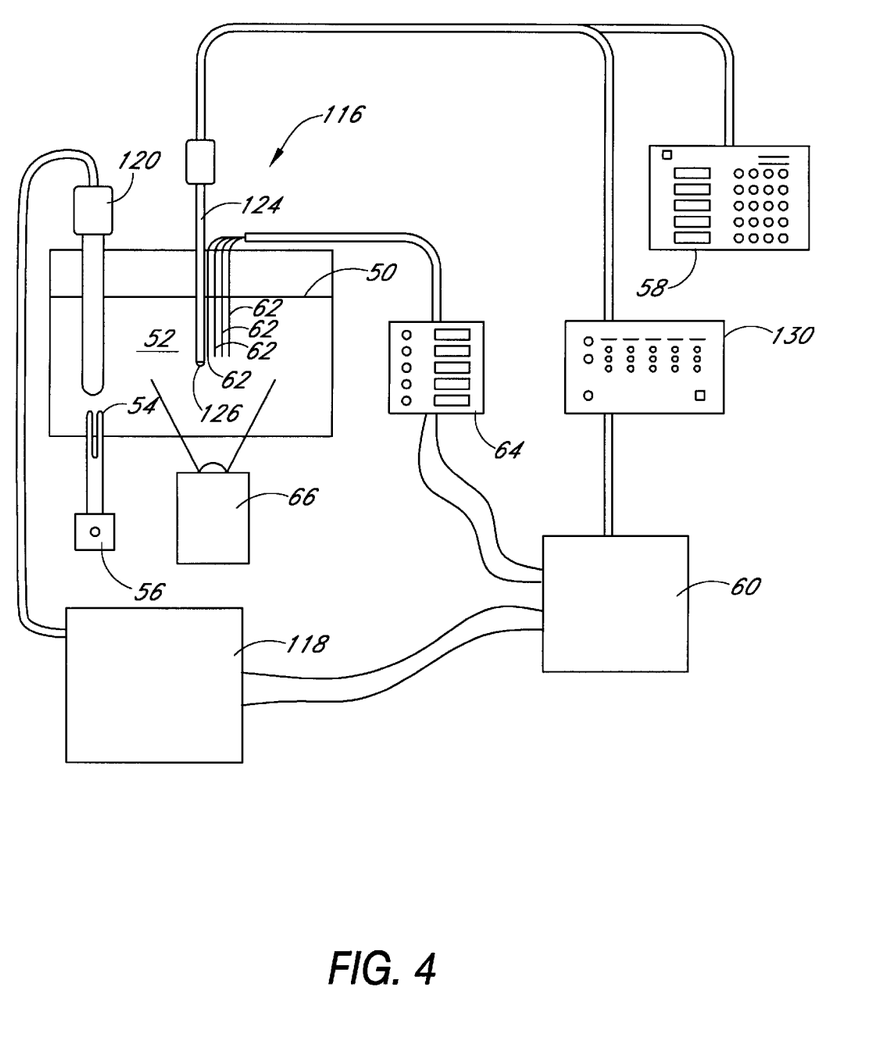
FIG. 4 is a block diagram of an empirical test which may be used to gather data for use in predicting the extent of tissue manipulation in a surgical setting.

FIG. 4 illustrates a set up which may be used to develop empirical data for the use by the analysis system 48. Measurements of manipulation process parameters are made using a chamber 50 of gel 52, with similar chemical and physical properties as substance which is to be manipulated. For example, the gel 52 may have the same colloidal and thermal properties of tissue as discussed in the NASA Brief Volume 92, page 56 data January 1992, entitled "Tissue Simulating Gel for Medical Research". The gel 52 is preferably maintained at 37 degrees Celsius by a heat exchanger 54 in the gel connected to a temperature controller 56.

A manipulation device 116 causes a thermal change in the area surrounding the tip of the shaft 124. The manipulation device 116 is connected to a source 58 for controlling the manipulation process. A receiver 126 is disposed at the tip a shaft 124 of the manipulation device 116. The receiver 126 is used to measure the radiated signal level during the test process. The receiver 126 is connected to a signal recovery unit 130. The signal recovery unit 130 receives a response signal from the receiver 126 and produces a signal level indication. The value of the signal level indication is measured and logged by a data recording system 60.

In the present example, the measure of manipulation is the measure of tissue destruction. Tissue destruction is a function of the temperature the tissue. Therefore, measurement of the change in temperature over time as a function of the distance from the tip of the device shaft 124 is made using a series of thermocouples 62. The thermocouples 62 are connected to a measurement system 64 which determines the temperature of the thermocouples 62 as a function of time. During the manipulation process, the temperature changes within the gel are logged by the data recording system 60. These temperature measurements create a profile of temperature changes as a function of distance and time.

Simultaneously, a scanner 120 of an ultrasound imaging system 118 emits a radiated signal in order to produce an image of the manipulated gel. The scanner 120 is placed in the gel 52 in proximity to the manipulation device 116 to allow the field of view of the scanner 120 to include the entire zone of gel manipulation. The resultant signal from the scanner 120 is passed to the ultrasound imaging system 118 which produces and displays image data which is recorded by the data recording system 60. A video camera 66 is directed at the manipulation device 116 and may also be used to record visual changes in the length or width of the zone of gel 52, manipulated by the device 116.

Figure 5A:
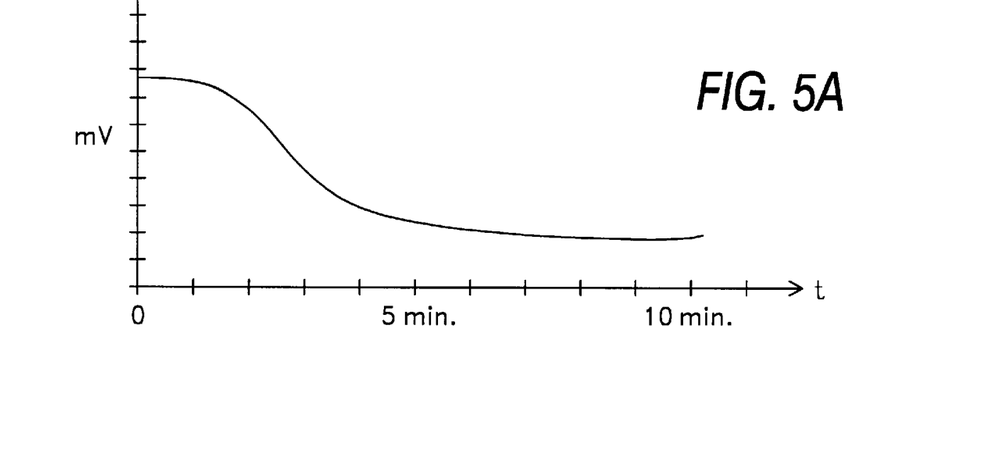
FIGS. 5A, 5B and 5C are a series of graphs illustrating exemplary data collected by the system of FIG. 4 when the manipulation process involves the removal of thermal energy.
Figure 5B:
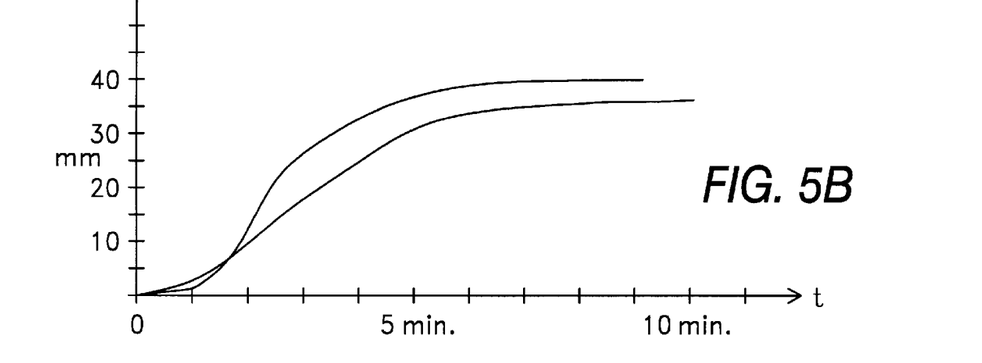
Figure 5C:
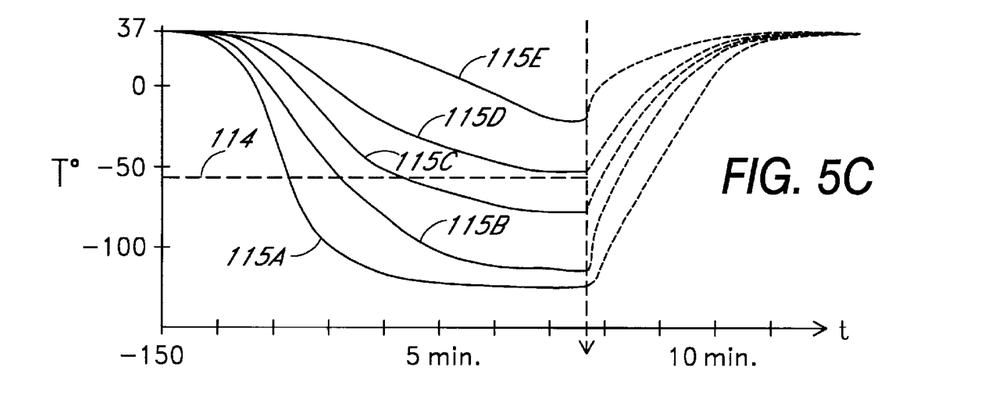

The information recorded by the data recording system 60 is compiled and used to create a model of the time, distance, and degree of manipulation of the gel 52 by the device 116. Typical measurements used to create the model of a cryosurgical manipulation are shown in FIGS. 5A–C. FIG. 5A shows the signal level indication in millivolts as a function of time received by the signal recovery unit 130 from the receiver 126. In this case, the level in millivolts is decreasing to reflect the fact that the signal level received by the receiver 126 from the scanner 120 is decreasing.

FIG. 5B shows a typical plot of the length and width of the image of the iceball as a function of time measured by the video camera 66 or the ultrasound imaging system 118. Measurements by the video camera 66 produce a recording of a visual change between the manipulated and unmanipulated gel. In the case of the cryomanipulation, FIG. 5B is a recording of the interface of the phase change caused by the manipulation device 116. The video camera 66 measures the border of the frozen gel as it expands due to the continued manipulation of the manipulation device 116. Other types of manipulation, such as heating and drug injection, that cause visual differences within the gel as a result of manipulation can also be measured. Measurements by the scanner 120 of the ultrasound imaging system 118 produce a recording of the acoustic boundary between the manipulated and unmanipulated gel. In the case of cryomanipulation, FIG. 5B is a recording of the density change between the frozen and unfrozen gel. Other types of manipulation, such as heating or injection of echogenic substances, that create acoustic interfaces within the gel that can be measured by the scanner 120 of the ultrasound imaging system 118 are possible. The manipulation zone is typically not perfectly spherical and, therefore, the length and width of the area of manipulated gel are not the same.

FIG. 5C is a graph representing the cryomanipulation of the gel and shows the measurement of one parameter, temperature, at fixed distances from the source of manipulation as a function of time. For example, a curve 115A represents the temperature at a distance of 5 mm from the tip of the probe 116. A curve 115B represents the temperature at a distance of 7.5 mm from the tip of the probe 116. In a like manner, the curves 115C–E represent the temperature at a distance of 10, 12.5, and 15 mm from the tip of the probe 116 respectfully. From the curves 115A–E, a determination of the relationship between temperature, distance, and time may be made for one level of manipulation. Similar curves may be obtained for different levels of manipulation. Different parameters, such as water content, pH, drug or marker levels, may also be measured depending on the nature of the manipulation source.

The model created from these measurements can then be used to predict the extent of tissue manipulation in a patient during the clinical use of the manipulation device. In the example of cryosurgical manipulation of tissue, we assume that tissue destruction occurs at approximately minus 60 degrees Celsius. From the model described above for the cryomanipulation of a gel with similar thermal properties as tissue, we can predict how long it takes tissue at various distances from the probe using FIG. 5C to reach minus 60 degrees Celsius. A horizontal line 114 shows a temperature of minus 60 degrees Celsius. Thus, at 5 mm from the probe, tissue reaches minus 60 degrees Celsius in about 2 minutes and 20 seconds. At 7.5 mm from the probe, tissue reaches minus 60 degrees Celsius in about 3 minutes and 20 seconds. At 10mm from the probe, tissue reaches minus 60 degrees Celsius in about 4 minutes and 30 seconds. After about 8 minutes, tissue reaches minus 60 degrees Celsius just under 12.5 mm in diameter according to curve 115D. However, note that the iceball dimension which would be detected by a ultrasonic imaging device is nearly 35 mm in diameter after 8 minutes as shown in FIG. 5B, thus illustrating the boundary of the scanned image does not correspond to a temperature indicative of tissue destruction.

The foregoing example clearly indicates that ultrasound or visual measurement of tissue changes alone does not provide sufficient information to reliably predict the extent of tissue manipulation. However, the model just described provides a powerful tool to predict the temperature profile within a zone of manipulated tissue from one parameter, such as the iceball boundary. In one embodiment, the invention predicts the area within the zone of manipulated tissue that has reached minus 60 degrees Celsius in relationship to the manipulation device, the iceball boundary, and other landmarks within the field of view of the ultrasound imaging system. Thus, the surgeon can more accurately manipulate the desired tissue.

If other means of manipulation are used, analogous tests must be made. It may also be necessary to run tests with varying distances and with varying levels of obstruction between the probe and the scanner. The data retrieved by this process may be stored within a database within the imaging and analysis system 40.

Figure 6:
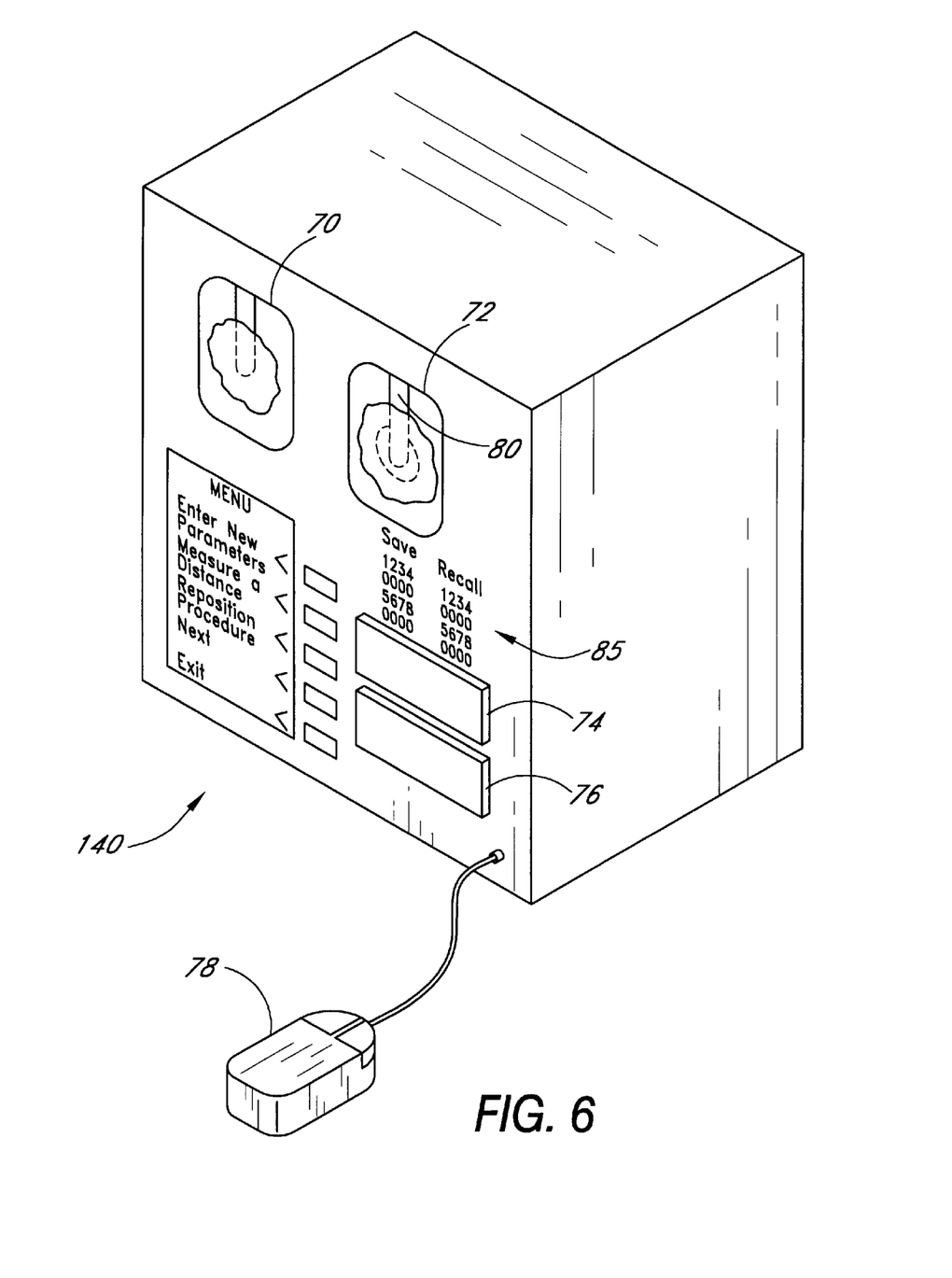
FIG. 6 is an elevational view of an exemplary embodiment of the imaging and analysis system.

FIG. 6 is a perspective view of an exemplary embodiment of the imaging and analysis system 40. In the preferred embodiment, the means used to perform the imaging and analysis function are a combination of hardware and software components. The implementation of the means may be a general purpose microprocessor which executes stored code. The means may also comprise one or more application specific integrated circuits. Alternatively, the means may operate on a general purpose, personal computer.

In FIG. 6, the real time signal derived from the scanner 20 is displayed in a frame 70. A second frame 72 is used for diagnostics. The second frame 72 may be used to display the results of the imaging and analysis system 40 or to allow the user to input desired control functions. The operator has the ability to display several images on the second frame 72 such as a stored image, a freeze frame, or the real time display as shown on the frame 70. Input controls 85 allow the operator to choose, save and recall a number of images from the frame 70 to display in the second frame 72. Any manner of other user-friendly features may be provided such as direct screen measurement of the physical dimension of the images on the screen. In FIG. 6, a control 74 allows the operator to control these and other features. In FIG. 6, a computer mouse 78 is also shown as part of the user interface. Any manner of user interface may be used consistent with the present invention.

The imaging and analysis system 40 also employs the second frame 72 to display the results of its analysis. For example, the imaging and analysis system 40 may use empirical data to predict the extent of manipulation including tissue destruction, viability, temperature, or density at various locations shown in the image of the second frame 72. The information may be derived from empirical tests such as described above. The empirical results are correlated with the image on the screen with relation to an identifiable landmark within the tissue. The landmark may be identified by the operator or the imaging and analysis system 40 and may be the receiver 26. The predicted parameters may be displayed by superimposing an image on the second frame 72 such as markers, boundaries, or colors. Alternate embodiments of the imaging and analysis system 40 may use mathematical equations such as quadratic equations or Fourier transforms, or other computational means to predict the extent of manipulation.

The display of the predicted manipulation on the second frame 72 can be updated based upon the signal received by the receiver 26 during the manipulation process. The operator may use the updated information to adjust the manipulation process to achieve the desired therapeutic result.

Alternatively, the imaging and analysis system 40 may be linked to the control of the manipulation process and effect manipulation adjustments directly. Control of the manipulation process may be entered by the operator through the control input 76. The control input 76 provides a means for the operator to input a desired therapeutic goal at a particular tissue location, such as a desired temperature, viability, density or other manipulative parameter. The imaging and analysis system 40 uses the analysis process just described to control the manipulation process to achieve the desired result. During the process, the second frame 72 may display the extent to which the desired result has been achieved.

Figure 7:
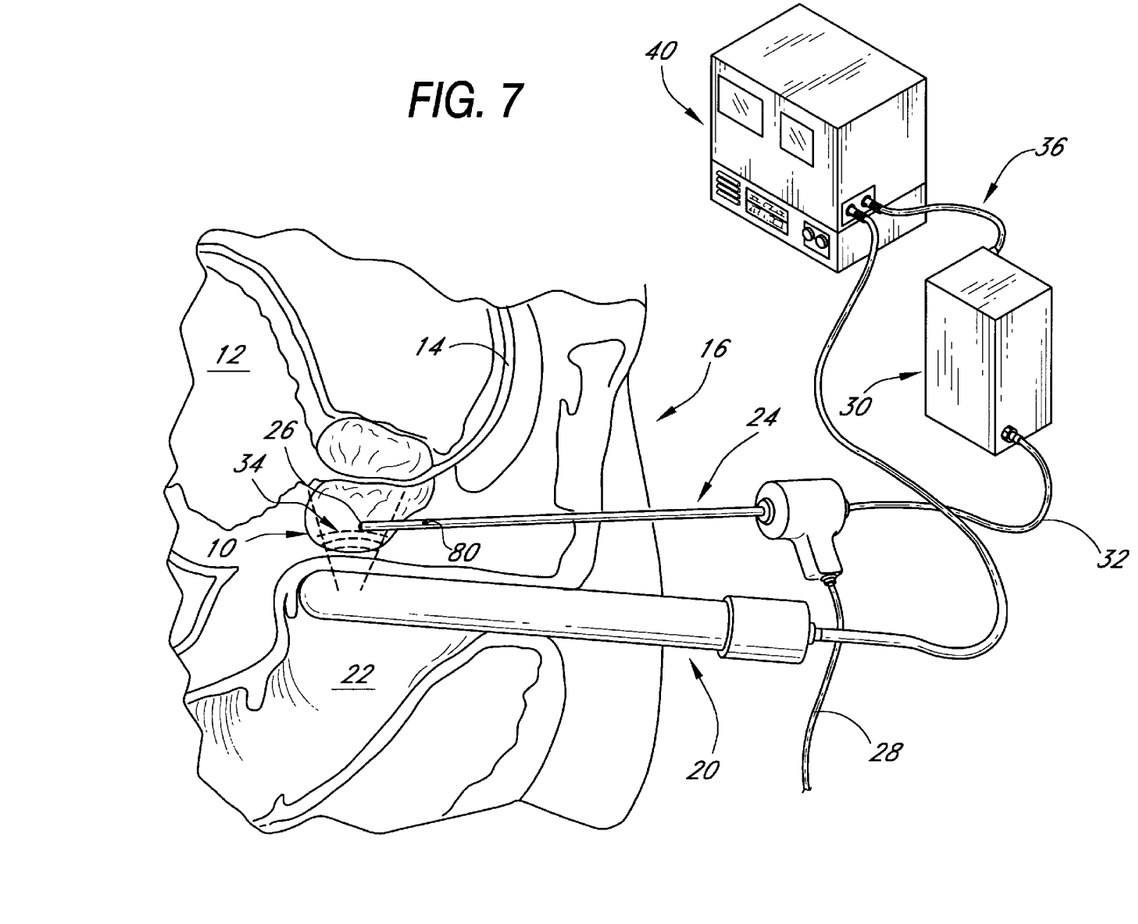
FIG. 7 illustrates an embodiment of the present invention which includes a second receiver to facilitate the positioning of the first component in relationship to the second component.

An alternate embodiment of the inventive system which addresses the issue of movement of the receiver or scanner during the manipulation process is illustrated in FIG. 7. As discussed supra, the signal received by the receiver 26 during the manipulation process is a function of the distance between the receiver 26 and the scanner 20 as well as the characteristics of the intervening tissue, organs or bone etc. A change in the relative position between the scanner 20 and the receiver 26 during the manipulation process affects the signal received by the receiver 26. If the system experiences a change in the signal level due to relative movement between the scanner 20 and the receiver 26, the analysis which estimates the extent manipulation becomes flawed.

During the manipulation procedure, the receiver 26 and scanner 20 are typically fixed in position and compensation for relative movement is not an issue. However, in situations where the scanner 20 or receiver 26 is purposefully or accidentally moved during the manipulation procedure, returning the device to its original position can be difficult and, yet, critical to accurately manipulating the tissue.

The presence of a second receiver 80 outside the zone of manipulated tissue, but receiving a detectable incident from the scanner 20, facilitates the repositioning of the receiver 26 or the scanner 20 during the manipulation process. In FIG. 7, the second receiver 80 is shown attached to the shaft 24 of the manipulation probe 16. Other embodiments of the inventive concept may be arranged to position the second receiver 80 on a needle placed in tissue or attached to the skin surface. The limiting factor for the second receiver 80 is that it must receive signals from the scanner 20.

Through the use of the second receiver 80, the imaging and analysis system 40 can record the signal level indication received at the first receiver 26 and the second receiver 80. The signal level indication is a function of both the distance between the scanner 20 and the receivers 26 and 80 and the characteristics of the intervening tissue. Therefore, in order for both of these parameters to return to the stored values, both the distance and the tissue characteristics between the receivers 26 and 80 and the scanner 20 must return to their original values before the imaging and analysis system 40 indicates that the probe and scanner have been properly replaced.

A physician may use the invention just described in order to determine a measure of manipulation during the course of a tissue manipulation process. The physician disposes a manipulation probe within an area of tissue. A measurement of a signal strength of a radiated signal received within the zone of manipulation is made. A determination of an extent of manipulation of the tissue based on the signal strength is made. In one embodiment, the process of determining the extent of manipulation is executed by determining a distance between a radiated energy source and a receiver within the zone of manipulation, measuring an initial value of the signal strength, and correlating the distance, the initial value of the signal strength and a subsequent value of the signal strength in order to determine the extent of manipulation. The correlation process may comprise the step of consulting a database of entries determined from empirical data in a manner such as the one detailed above.

In order to visualize the area of manipulation, the physician may insert a radiation source within a patient such as an ultrasound imaging device adapted for insertion into the rectum as shown in FIG. 1. Once properly positioned, in one embodiment, the physician destroys a portion of the area of tissue by addition of energy from the tip of the manipulation probe. In another embodiment, the physician destroys a portion of the area of tissue by removal of energy through the tip of the manipulation probe. For example, the physician may destroy a portion of the area of tissue comprising diseased prostatic tissue.

During the manipulation process, an image prediction of the extent of manipulation is displayed for the physician, for example, as shown in FIG. 6. In one embodiment the image of the area of tissue is derived from signals returning from a source of the radiated energy such as from an ultrasound imaging device adapted for insertion into the rectum.

In one embodiment, in order to use the repositioning feature described above, a measurement of a signal strength of the radiated signal received at a point on the probe offset from the first receiver so as to be outside of the area of tissue may be taken. A determination of a previous location of the probe or scanner based on the signal strength of the radiated signal measured at the point on the probe offset from the first receiver is made. For example, a measurement of an initial signal strength received at a point outside of the area of tissue may be stored for later use. In the event the probe or the imaging system is moved, the physician may reposition the radiated energy source such that a new signal strength received at the point outside of the area of tissue is approximately equal to the initial signal strength.

In summary, the physician inserts a manipulative probe such that it may manipulate a region of diseased tissue. A measurement of a signal strength of a radiated field at the probe is made. The physician begins manipulation the region of diseased tissue by application of a manipulative force. The physician terminates manipulation of the region of diseased tissue when the signal strength reaches a predetermined value.

The invention may be implemented in a wide variety of forms. For example, brachytherapy treats tissue by the implantation of radiation beads within an area of manipulation. A probe is used to place the radiation beads at predetermined positions within the area of manipulation. After positioning the beads, the operator removes the probe, leaving the beads in place. Accurately positioning the beads is critical to optimally destroying all diseased tissue within the area of manipulation. In order to incorporate the invention into brachytherapy, a receiver is positioned within the area of manipulation. In the same manner described above, the receiver aids in visualization of the extent of manipulation of tissue. The analysis of the extent of tissue manipulation caused by the beads allows the operator to adjust the position to optimize diseased tissue destruction or prevent undesirable destruction of healthy tissue.

The general principles of the invention were described in relation to a specific embodiment above. However, the general principles of the present invention are not limited to the specific example above. For example, the process above was described with reference to a freezing process in which energy is removed from an area of tissue. The invention provides similar advantages if energy is added to the area such as by the application of thermal heat, RF energy, gamma rays or other method. A variety of substances may also be used in the process of manipulating tissue in conjunction with the present invention. For example, chemotherapeutic drugs for the treatment of cancer, photodynamic substances for the destruction of tissue, collagen for altering the geometry of a space, or other agents, chemical or physical, may be used to cause manipulation. In addition, a mechanical means of manipulation may be used such as beaters or blades or other means to emulsify tissue or by injection or removal of water. In general, manipulation within the meaning of the present invention refers to any influence on the tissue—whether the manipulation destroys, enhances, removes or otherwise affects the tissue. Whatever method of manipulation is chosen, empirical data can be collected using methods similar to those described above. The resulting data may be used in the analysis process. It is also noted that the some means of manipulation such as heating the tissue may increase, rather than decrease, the signal level indication value. However, the process of the collecting and correlating data is the same.

In the example above, the invention is described with reference to an ultrasound radiated signal. According to the principles of the present invention, other types of radiated signals could be used such as X-rays, high frequency radio waves, microwaves, electromagnetic energy or other later developed means of providing an incident signal in order to produce an image.

In the example above, the receiver is disposed at the tip of a probe because it is the tip of the probe which provides the means of manipulation. However, location at the tip of a probe, or even on the probe itself, is not critical. The advantages of the present invention are gained by locating the receiver within the area of manipulation. In a configuration in which the manipulation occurs along the length of a needle, probe, catheter or other device, the receiver may be disposed along the length of the device also. Likewise, the term 'probe' as used herein can be one of many sorts of devices such as needles, catheters, implantation devices or the like. The probe is simply the means by which the manipulation means or the receiver is disposed within the area of diseased tissue.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. A surgical device for use with an ultrasound transmitter, said surgical device comprising:
   a probe adapted for insertion into a patient, said probe comprising means for manipulating tissue within a zone of manipulation;
   a first receiver disposed within said zone of manipulation, wherein said first receiver responds to receipt of a diagnostic ultrasound signal by generation of a first receiver signal indicating a strength at which said diagnostic ultrasound signal is received; and
   means for analyzing said first receiver signal to determine a measure of manipulation to the tissue within said zone of manipulation.

2. The surgical device of claim 1, wherein said first receiver is disposed at a tip of said probe.

3. The surgical device of claim 1, wherein said means for manipulating removes energy from the tissue.

4. The surgical device of claim 1, wherein said means for manipulating manipulates tissue by introduction of a substance.

5. The surgical device of claim 1, wherein said means for manipulating manipulates tissue by introduction of a fluid.

6. The surgical device of claim 1, wherein said means for manipulating manipulates the tissue through a mechanical means.

7. The surgical device of claim 1, wherein said means for analyzing accumulates a set of values of said first receiver signal over time in order to determine said measure of manipulation.

8. The surgical device of claim 1, wherein said probe implants said means for manipulating tissue within the patient.

9. The surgical device of claim 8, wherein said means for manipulating tissue is a bead.

10. A surgical device comprising:
    a probe adapted for insertion into a patient, said probe comprising means for manipulating tissue within a zone of manipulation;
    a first receiver disposed within said zone of manipulation, wherein said first receiver responds to receipt of a diagnostic ultrasound signal by generation of a first receiver signal indicating a strength at which said diagnostic ultrasound signal is received;
    means for analyzing said first receiver signal to determine a measure of manipulation to the tissue within said zone of manipulation; and
    a scanner generating said ultrasound signal.

11. The surgical device of claim 10, wherein said scanner is disposed within the patient.

12. The surgical device of claim 10, wherein said scanner is external to said patient.

13. The surgical device of claim 10, wherein said means for analyzing comprises an imaging system for displaying an image derived from signals generated by said scanner.

14. The surgical device of claim 13, wherein said means for analyzing further comprises a database comprising entries determined by empirical measurement and wherein said means for analyzing consults said database to determine said measure of manipulation.

15. The surgical device of claim 13, wherein said means for analyzing displays a predication of said measure of manipulation.

16. The surgical device of claim 15, wherein said means for analyzing superimposes said prediction over said image derived from said signals generated by said scanner.

17. The surgical device of claim 10, wherein said means for analyzing comprises:
    means for determining a distance between said scanner and said first receiver;
    means for measuring an initial value of said first receiver signal; and
    means for correlating said distance, said initial value of said first receiver signal and a subsequent value of said first receiver signal to determine said measure of manipulation.

18. The surgical device of claim 17, wherein said means for correlating comprises a database of entries determined from empirical data.

19. A method of determining a measure of manipulation comprising the steps of:
    disposing a manipulation probe within an area of tissue manipulating the tissue with said manipulation probe;
    measuring a signal strength of a diagnostic ultrasound signal received at a receiver on said manipulation probe from an ultrasound scanner; and
    determining the extent of manipulation of the tissue based on said signal strength.

20. The method of claim 19, wherein said step of determining said extent of manipulation comprises the steps of:
    determining a distance between said ultrasound scanner and said receiver;
    measuring an initial value of said signal strength; and
    correlating said distance, said initial value of said signal strength and a subsequent value of said signal strength in order to determine said extent of manipulation.

21. The method of claim 20, wherein said step of correlating further comprises the step of consulting a database of entries determined from empirical data.

22. The method of claim 21, further comprising the step of inserting a radiation source within a patient.

23. The method of claim 19, further comprising the step of manipulating a portion of said area of tissue by introduction of a substance.

24. The method of claim 19, further comprising the step of manipulating a portion of said area of tissue by introduction of a fluid.

25. The method of claim 19, further comprising the step of destroying a portion of said area of tissue by removal of energy.

26. The method of claim 19, further comprising the step of manipulating a portion of said area of tissue by destroying the tissue with a mechanical means.

27. The method of claim 19, further comprising the step of displaying an image prediction of said extent of manipulation.

28. The method of claim 27, further comprising the step of displaying an image of said area of tissue derived from signals returning from a source of said ultrasound signal.

29. The method of claim 19, wherein said ultrasonic scanner is disposed within the patient to produce said ultrasound signal.

30. A method of accurately destroying diseased tissue in a non-invasive surgical procedure using an ultrasound scanner, said method comprising the steps of:

inserting a manipulative probe into a patient such that a manipulation means of said probe is disposed within a region of diseased tissue;

measuring a signal strength of a diagnostic ultrasound signal within said region of diseased tissue;

beginning manipulation said region of diseased tissue; and terminating manipulation of said region of diseased tissue when said signal strength reaches a predetermined value.

31. A test device for correlation of image results to actual results in a system for manipulation comprising:

a detector for detection of an ultrasound signal;

a manipulation generator generally co-located with said detector;

a series of measurement units distributed at a variety of distances from said detector, said series of measurement units for measuring an indication of a degree of manipulation;

an ultrasound signal generator for generating said diagnostic ultrasound signal; and a recording device coupled to said series of measurement units and said detector;

wherein said detector, said manipulation generator and said series of measurement units are disposed within an artificial in vitro material having similar physical and chemical properties of soft tissue and wherein said recording device is used to record input from said detector and said series of measurement units during manipulation of said material by said manipulation generator.

* * * * *

UNITED STATES PATENT AND TRADEMARK OFFICE
CERTIFICATE OF CORRECTION

PATENT NO.    : 6,083,166
DATED         : July 24, 2000
INVENTOR(S)   : Holdaway et al.

Page 1 of 1

It is certified that error appears in the above-identified patent and that said Letters Patent is hereby corrected as shown below:

<u>Column 5,</u>
Line 16, cancel "t" and replace it with -- the --.

Signed and Sealed this

Second Day of April, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,083,166
DATED : July 4, 2000
INVENTOR(S) : Holdaway et al.

It is certified that error appears in the above-identified patent and that said Letters Patent is hereby corrected as shown below:

Column 5,
Line 16, cancel "t" and replace it with -- the --.

This certificate supersedes Certificate of Correction issued April 2, 2002.

Signed and Sealed this

Twentieth Day of August, 2002

Attest:

Attesting Officer

JAMES E. ROGAN
Director of the United States Patent and Trademark Office